US00PP35468P2

(12) United States Plant Patent
Rubio-Cabetas et al.

(10) Patent No.: US PP35,468 P2
(45) Date of Patent: Nov. 14, 2023

(54) ***PRUNUS* ROOTSTOCK NAMED 'PILOWRED'**

(50) Latin Name: ***Prunus amygdalus* x *persica***
Varietal Denomination: Pilowred

(71) Applicant: Agrifood Research and Technology Center of Aragon, Saragossa (ES)

(72) Inventors: Maria Jose Rubio-Cabetas, Saragossa (ES); Antonio Felipe Mansergas, Saragossa (ES)

(73) Assignee: Agrifood Research and Technology Center of Aragon

( * ) Notice: Subject to any disclaimer, the term of this patent is extended or adjusted under 35 U.S.C. 154(b) by 0 days.

(21) Appl. No.: 18/085,408

(22) Filed: Dec. 20, 2022

(51) Int. Cl.
*A01H 5/08* (2018.01)
*A01H 6/74* (2018.01)

(52) U.S. Cl.
USPC ..... Plt./156

(58) Field of Classification Search
USPC ..... Plt./183, 155, 180, 156
See application file for complete search history.

(56) References Cited

PUBLICATIONS

Montesinos et al. "Proleptic and Sylleptic Shoot Formation Is Affected by Rootstock Genotype in Two-Year Old Branches of Almond Trees," Agronomy 2022, 12, 2006, pp. 1-8; published Aug. 25, 2022.*

* cited by examiner

*Primary Examiner* — Susan McCormick Ewoldt
(74) *Attorney, Agent, or Firm* — Cassandra Bright

(57) ABSTRACT

A new and distinct *Prunus* rootstock named 'Pilowred' is disclosed, characterized by early bearing and early fruiting as well as root-knot nematode (RKN) resistance. The new rootstock imparts low vigor. Foliage is colored intermediate red. The new variety is a *Prunus amygdalus* x *persica*, for use as a commercial rootstock.

3 Drawing Sheets

Latin name of the genus and species: *Prunus amygdalus* x *persica.*

Variety senomination: 'Pilowred'.

BACKGROUND OF THE INVENTION

The new cultivar is a product of a planned breeding program conducted by the inventors in Zaragoza, Spain. The purpose of the breeding program was to develop *Prunus* rootstocks with root-knot nematode (RKN) resistance, reduced vigor and red leaf color. The breeding program began in 1987, parent varieties of 'Pilowred' are *Prunus amygdalus* 'Garfi', unpatented (female) x *Prunus persica* 'Nemared', unpatented (male). The new variety was selected during 2015 as an individual tree demonstrating the desired characteristics. The trial orchard is located in Zaragoza, Spain.

Asexual reproduction of the new cultivar 'Pilowred' was first performed via tissue culture in a commercial laboratory in Zaragoza, Spain during 2015. Subsequent propagation has shown that the unique features of this cultivar are stable and reproduced true to type on successive generations. At the time of this filing no commercial sales have taken place.

SUMMARY OF THE INVENTION

The cultivar 'Pilowred' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Pilowred'. These characteristics in combination distinguish 'Pilowred' as a new and distinct *Prunus* cultivar:

1. The rootstock has shown root-knot nematode (RKN) resistance.
2. Intermediate red foliage color.
3. Imparts low vigor.
4. Early bearing.
5. Early fruiting.

PARENT COMPARISON

Plants of the new cultivar 'Pilowred' are similar to plants of the seed parent, in most horticultural characteristics, including drought tolerance and general efficiency of water use. Trees of the new cultivar 'Pilowred', however, differ in the following:

1. Trees of the new cultivar grow significantly less vigorously.
2. Trees of the new cultivar have a more controlled growth habit.
3. Foliage of the new cultivar is intermediate red; foliage of the seed parent is green.

Plants of the new cultivar 'Pilowred' are similar to plants of the pollen parent in most horticultural characteristics, including observed RKN resistance. Plants of the new cultivar 'Pilowred', however, differ in the following:

1. Trees of the new cultivar grow significantly less vigorously.
2. Trees of the new cultivar have a more controlled growth habit.

COMMERCIAL COMPARISON

Plants of the new cultivar 'Pilowred' are similar to plants of the known commercial variety 'Rootpack20', in most horticultural characteristics, however, plants of the new cultivar 'Pilowred' differ in the following:

1. Trees of 'Pilowred' flower 7 days earlier than this comparator.
2. Trees of 'Pilowred' require less 120 of chilling than this comparator.
3. Trees of 'Pilowred' have intermediate red colored foliage; trees of this comparator have green foliage.

BRIEF DESCRIPTION OF THE PHOTOGRAPHS

The accompanying photographs in FIG. 1 through FIG. 3 illustrate in full color typical trees of 'Pilowred' grown in at a research nursery in Zaragoza, Spain. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Prunus* tree. No artificial light, photoperiodic treatments or chemical treatments were given to the plants.

DETAILED BOTANICAL DESCRIPTION

Figure 1:
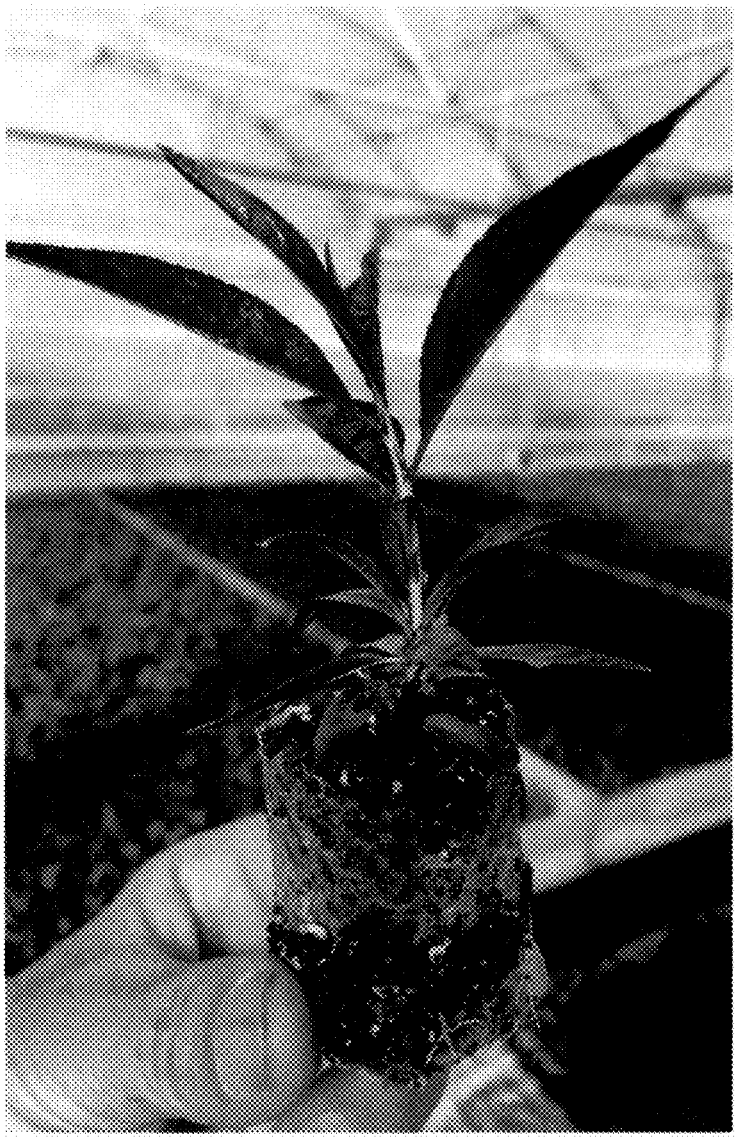
FIG. 1 illustrates in full color a newly planted rootstock plug.
Figure 2:
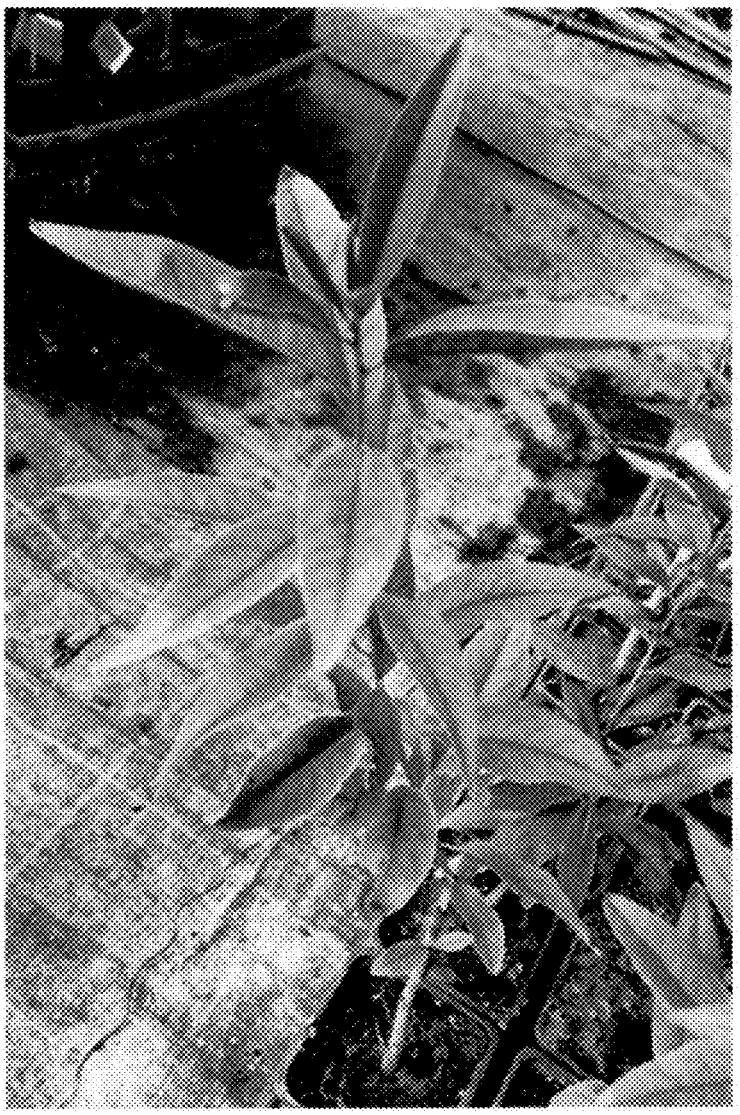
FIG. 2 illustrates in full color a young plant in a 5 cm pot.
Figure 3:
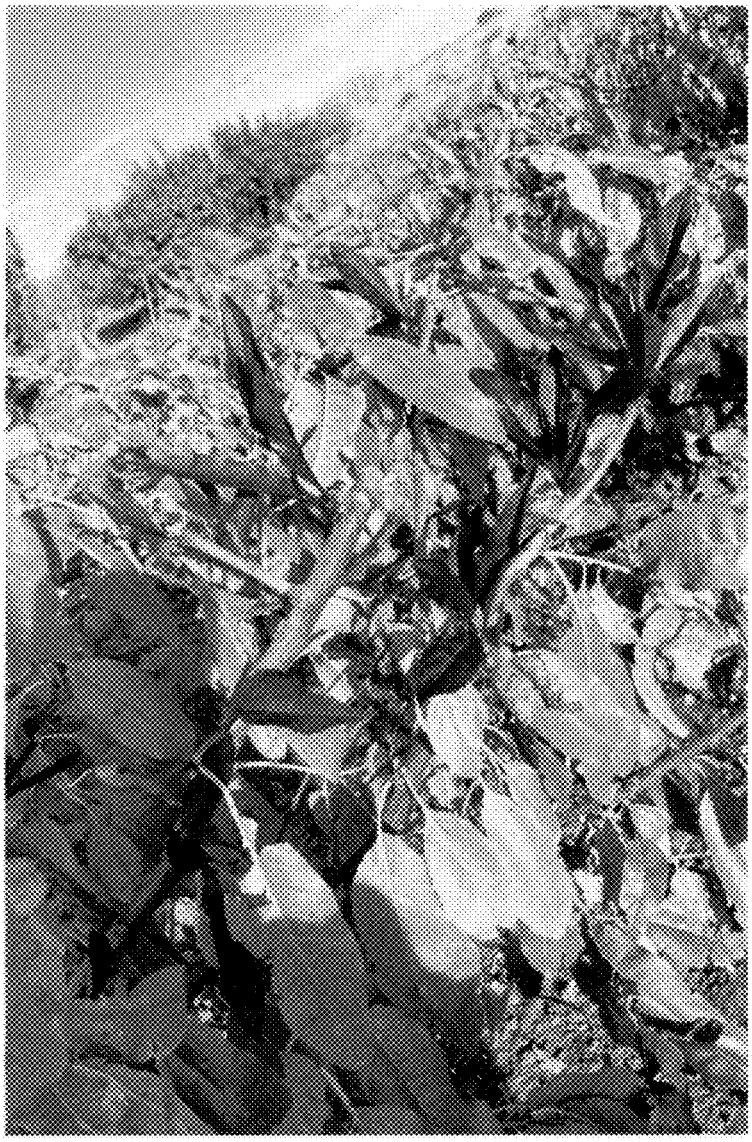
FIG. 3 illustrates in full color a mature tree which has been pruned and is beginning to grow back.

In the following description, color references are made to The Royal Horticultural Society Colour Chart 2015 except where general terms of ordinary dictionary significance are used. The following observations and measurements describe 'Pilowred' plants grown outdoors in Zaragoza, Spain. Growing conditions are similar to USDA Zone 9. Measurements were taken from a mature tree of 15 years. Measurements and numerical values represent averages of typical plant types at corresponding age of maturity.

Botanical classification: *Prunus amygdalus* x *persica* 'Pilowred'.

TREE

Time of year measurements taken: September.
Height: Approximately 2.15 meters at 15 years.
Plant spread: Approximately 2 meters.
Density: Medium.
Form: Broad orbicular with branching angles less than 65 degrees from center.
Bearing: Apical.
Vigor: Low.
Growth habit: Upright, deciduous tree.
Suckering: No presence of root sprouts or spurs.
Anchorage: Strong.
Compatibility: Good.
Branching characteristics:
- *Diameter.*—9.4 mm at 1 m from the apex of a one-year branch.
- *Texture.*—Smooth.
- *Color.*—Near RHS Red-Purple 59A for anthocyanin coloration of the sun exposed zone and N144D for the rest of the branch.
- *Aspect.*—Moderate curve. Average angle 50 degrees.
- *Lenticels.*—Length: 0.2 mm. Width: 0.2 mm. Shape: round. Density: 5 lenticels per $cm^2$. Color: Near RHS Yellow-Green 159D.

Trunk:
- *Circumference.*—Approximately 17.89 at 5 cm from ground level.
- *Texture.*—Rough.
- *Color.*—Near Greyed-Purple 189B.
- *Lenticels.*—Density: Approximately 18 per $cm^2$. Lenticel length: Approximately 1 mm. Lenticel width: Approximately 0.3 mm. Lenticel color: Near RHS Yellow-White 158B.

FOLIAGE

Leaf:
- *Arrangement.*—Alternate.
- *Length.*—Average 12 cm.
- *Width.*—Average 4 cm.
- *Shape.*—Elliptic
- *Attachment.*—Petiolate.
- *Apex.*—Acute.
- *Base.*—Tapered.
- *Margin.*—Crenate.
- *Texture of top surface.*—Glabrous veins not prominent.
- *Texture of bottom surface.*—Glabrous.
- *Color.*—Young foliage upper side: Near RHS Greyed-Purple 186A. Young foliage under side: Near RHS Greyed-Purple 186C. Mature foliage upper side: Near RHS Green 137B. Mature foliage under side: Near RHS Greyed-Purple 186C.
- *Venation.*—Type: Pinnate. Venation color: Upper Surface: Near RHS Green N137B. Lower Surface: Near RHS Greyed-Purple N185B.

Petiole:
- *Length.*—Approximately 1.5 cm.
- *Diameter.*—Approximately 1.55 mm.
- *Color.*—Near RHS Green 137B.
- *Texture.*—Smooth.

FLOWER

Flower buds:
Pedicel:
- *Length.*—1.76 mm.
- *Diameter.*—1.11 mm.
- *Color.*—Near RHS Yellow-Green 145A.

Bud:
- *Length.*—14.71 mm.
- *Width.*—9.66 mm.
- *Color.*—Near RHS Red-Purple 59B.

Flowers:
- *Bloom timing.*—February 24 in the year 2022 in Zaragoza, Spain.
- *General blooming period.*—Very early.
- *Number of flowers.*—0.4 flowers per cm of new branch.
- *Fragrance.*—Honey, medium-weak intensity.

Petals:
- *Number.*—5.
- *Length.*—20.31 mm.
- *Width.*—15.99 mm.
- *Shape.*—Rounded elliptic.

*Margin*.—Slightly undulated.
*Texture*.—Smooth.
*Color*.—When opening: Upper surface: Near RHS Red-Purple 62C. Lower surface: Near RHS Red-Purple 62C. Fully opened: Upper surface: Near RHS Red-Purple 62D. Lower surface: Near RHS Red-Purple 62D.

Sepals:
*Shape*.—Ovate.
*Margin*.—Entire.
*Texture*.—Lightly pubescent.
*Length*.—5.16 mm.
*Width*.—3.98 mm.
*Color*.—Upper surface: Near RHS Red-Purple 59B. Lower surface: Near RHS Red-Purple 59B.

REPRODUCTIVE ORGANS

Stamens:
*Number* (*per flower*).—46.
*Filament length*.—9.85 mm.

Anthers:
*Shape*.—Elliptic.
*Length*.—1.19 mm.
*Color*.—Near RHS Greyed-Orange 163A.
*Pollen*.—Color: Near RHS Yellow 7A. Amount (generally): Moderate.

Pistil:
*Quantity*.—1 per flower.
*Length*.—11.45 mm.

Style:
*Length*.—8.75 mm.
*Color*.—Near RHS Yellow-Green 145C.

Stigma:
*Shape*.—Ovate.
*Color*.—Near RHS Yellow-Green 145C.

OTHER CHARACTERISTICS

Fruit:
*Maturity when described*.—Phenological stage: 87. Fruit ripe for picking.
*Size*.—Diameter: 23.63 mm. Length: 28.98 mm.
*Skin*.—Thickness: 0.1 mm. Texture: Slightly wrinkled. Tendency to crack: No tendency. Color: Near RHS Yellow-Green 154D.
*Flesh*.—Aroma: None. Color: Near RHS Greyed-Orange 164A. Eating quality: Not applicable.
*Seeds*.—Number per fruit: 1. Length: 16.49 mm. Breadth: 12.39 mm. Form: Elliptic. Color: Near RHS Greyed-Orange 165A.

Disease resistance: Root-knot nematode (RKN) resistance.
Temperature tolerance: USDA Zone 9.
Drought tolerance: Drought tolerance observed.

What is claimed is:

1. A new and distinct cultivar of *Prunus* rootstock named 'Pilowred' as herein illustrated and described.

* * * * *